United States Patent [19]

Soo et al.

[11] Patent Number: 4,701,571
[45] Date of Patent: Oct. 20, 1987

[54] PROCESS FOR THE PRODUCTION OF ALKYLENE GLYCOLS WITH METALATE-CONTAINING SOLIDS

[75] Inventors: Hwaili Soo; John H. Robson, both of Charleston, W. Va.

[73] Assignee: Union Carbide Corporation, Danbury, Conn.

[21] Appl. No.: 880,032

[22] Filed: Jun. 30, 1986

[51] Int. Cl.⁴ .................... C07C 31/20; C07C 33/26; C07C 35/14; C07C 33/035
[52] U.S. Cl. .................... 568/867; 568/811; 568/833; 568/857
[58] Field of Search ................ 568/867, 833, 811, 857

[56] References Cited

U.S. PATENT DOCUMENTS

| 2,770,656 | 11/1956 | Pye | 568/867 |
| 4,551,566 | 11/1985 | Robson et al. | 568/867 |
| 4,560,813 | 12/1985 | Collier | 568/867 |
| 4,564,715 | 1/1986 | Briggs et al. | 568/867 |
| 4,571,440 | 2/1986 | Keen et al. | 568/867 |
| 4,578,524 | 3/1986 | Keen | 568/867 |
| 4,579,982 | 4/1986 | Briggs et al. | 568/867 |
| 4,579,983 | 4/1986 | Keen | 568/867 |

Primary Examiner—J. E. Evans
Attorney, Agent, or Firm—S. T. Trinker

[57] ABSTRACT

An improved process for the hydrolysis of alkylene oxide to produce alkylene glycol which comprises:
(a) reacting alkylene oxide and water in the presence of a selectivity-enhancing metalate-containing solid until about 90–95% of the alkylene oxide is converted to alkylene glycol; and
(b) completing the hydrolysis reaction of (a) in the absence of the selectivity-enhancing metalate-containing solid.

20 Claims, 1 Drawing Figure

DI Rate vs. EO Conversion

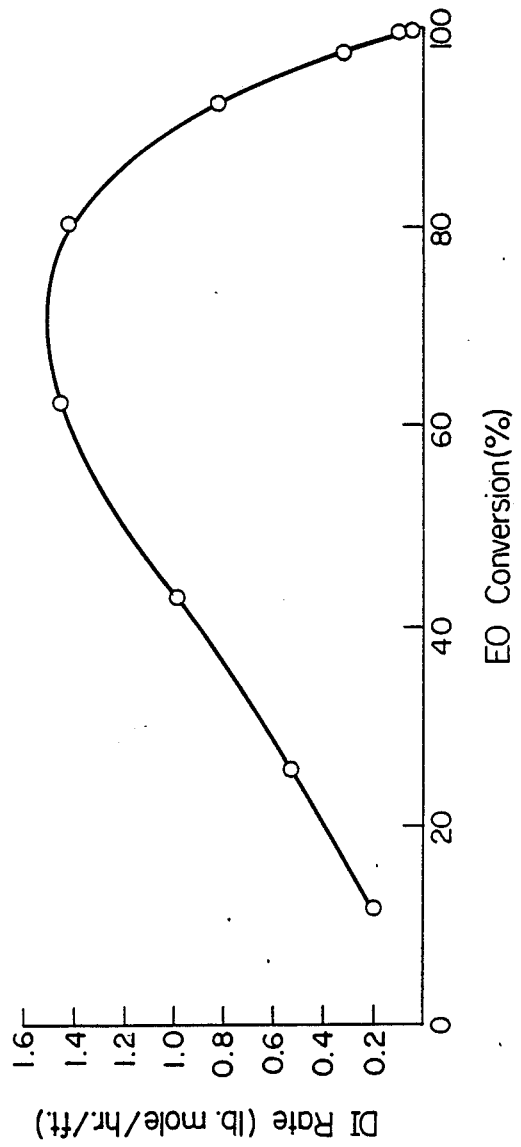

PROCESS FOR THE PRODUCTION OF ALKYLENE GLYCOLS WITH METALATE-CONTAINING SOLIDS

FIELD OF THE INVENTION

This invention relates to an improved process for the production of alkylene glycols from alkylene oxides and water in a heterogenous system. In particular, the present invention relates to an improved process for the production of alkylene glycols by hydrolysis of alkylene oxides which process reduces catalyst consumption without appreciable loss in alkylene glycol selectivity and yield.

BACKGROUND OF THE INVENTION

Commercial processes for the preparation of alkylene glycols, for example, ethylene glycol, propylene glycol and butylene glycol, involve the liquid-phase hydration of the corresponding alkylene oxide in the presence of a large molar excess of water (see, for example, Kirk-Othmer, *Encyclopedia of Chemical Technology*, Vol. 11, Third Edition, page 929 (1980)). The hydrolysis reaction is typically conducted at moderate temperatures, e.g., about 100 to about 200° C., with water being provided to the reaction zone in excess of 15 moles per mole of alkylene oxide. The primary by-products of the hydrolysis reaction are di- and polyglycols, e.g., dialkylene glycol, trialkylene glycol and tetra-alkylene glycol. The formation of the di- and polyglycols is believed to be primarily due to the reaction of alkylene oxide with alkylene glycol. As alkylene oxides are generally more reactive with alkylene glycols than they are with water, the large excesses of water are employed in order to favor the reaction with water and thereby obtain a commercially attractive selectivity to the monoglycol product.

Since the alkylene glycols must be recovered from the hydrolysis reaction mixtures, the large excess of water can result in an energy intensive procedure. Typically, the water is removed by evaporation to leave an alkylene glycol containing residue which is purified by distillation. Hence, a reduction in the amount of water employed while maintaining, or enhancing, selectivity toward the monoglycol product could be beneficial from the standpoint of energy efficiency.

The hydrolysis reaction proceeds uncatalyzed; however, the presence of acids or bases enhance the rate of reaction. Acid and base catalysts, however, do have shortcomings. For instance, base catalysts are generally not selective to the formation of the monoglycol product and acid catalysts are typically associated with corrosion problems. Hence, commercial processes typically utilize relatively neutral hydrolysis conditions (for instance, pH 6–10).

Representative of the numerous acid catalysts that have been suggested for use in the hydration of alkylene oxides include fluorinated alkyl sulfonic acid ion exchange resins (U.S. Pat. No. 4,165,440); carboxylic acids and halogen acids (U.S. Pat. No. 4,112,054); strong acid cation exchange resins (U.S. Pat. No. 4,107,221); aliphatic mono- and/or polycarboxylic acids (U.S. Pat. No. 3,933,923); cationic exchange resins (U.S. Pat. No. 3,062,889); acidic zeolites (U.S. Pat. No. 3,028,434); sulfur dioxide (U.S. Pat. No. 2,807,651); trihalogen acetic acids (U.S. Pat. No. 2,472,417); and copper-promoted aluminum phosphate (U.S. Pat. No. 4,014,945).

In addition to the acid catalysts, numerous catalysts have been suggested for the hydration of alkylene oxides in the presence of carbon dioxide. These include alkali metal halides, such as chlorides, bromides and iodides; quaternary ammonium halides such as tetramethyl ammonium iodide and tetramethyl ammonium bromide (British Patent No. 1,177,877); organic tertiary amines such as triethylamine and pyridine (German published patent application 2,615,595, and U.S. Pat. No. 4,307,256); quaternary phosphonium salts (U.S. Pat. No 4,160,116); and partially amine-neutralized sulfonic acid catalyst, e.g., partially amine neutralized sulfonic acid resin (U.S. Pat. No. 4,393,254).

Various metal containing compounds, including metal oxides, have been proposed as catalysts for the hydrolysis of alkylene oxides. For example, U.S. Pat. No. 2,141,443 discloses the production of glycols by the reaction of alkylene oxide with water in the presence of a dehydrating metal oxide, for example, alumina, thoria, or oxides of tungsten, titanium, vanadium, molybdenum or zirconium. The reaction is carried out in the liquid phase and under conditions of temperature and pressure suited to maintain such phase. In example 7, the patentees disclose rendering a yellow tungstic acid catalyst more mechanically stable by admixture with a mixture of silicon ester, alcohol and water followed by drying the catalyst. Similarly, U.S. Pat. No. 2,807,651 states that it is known to catalyze the reaction of an alkylene oxide and water by alkali metal bases, alcoholates, oxides of titanium, tungsten and thorium, certain metal salts such as $NiSO_4$, acid forming salts such as $BF_3$, and the chlorides of Zn, Sn, and Fe, certain hydrosilicates and acidified hydrosilicates such as aluminum hydrosilicate, lower alkyl tertiary amines (such as trimethyl, triethyl and triamyl), and certain organic salts such as diethylsulfate.

Compounds of many of the transition metals and other metals such as vanadium, molybdenum, tungsten, titanium, chromium, zirconium, selenium, tellurium, tantalum, rhenium, uranium and niobium, have also been proposed as components for catalysts for preparing 1,2-epoxides of alpha-olefins and organic hydroperoxides and often are present during a subsequent hydrolysis reaction. For instance, Examples I and III of U.S. Pat. No. 3,475,499 disclose that a mixture of normal alpha-olefins containing 11 to 15 carbon atoms was epoxidized with ethylbenzene hydroperoxide in the presence of molybdenum naphthanate catalyst. After distillation, the bottoms which contained the 1,2-epoxides and the molybdenum-containing catalyst were contacted with water containing 0.5 percent sodium hydroxide at a temperature of 90° C. That reaction product was distilled and a conversion of 1,2-epoxides was reported to be 100 percent and the selectivity to 1,2-glycols was reported to be 94 percent.

More recently, U.S. Pat. No. 4,277,632 discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by products such as the polyglycols. The reaction may be carried out in the presence of carbon dioxide; however, when the reaction is carried out in the presence of nitrogen, air, etc., the patentees state that the pH of the reaction mixture should be adjusted to a value in the range of 5 to 10.

Japanese Kokai No. JA 54/128,507 discloses a process for the production of alkylene glycols from alkylene oxides and water using metallic tungsten and/or tungsten compounds.

Japanese Kokai No. JA 56/073,035 discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids.

Japanese Kokai No. JA 56/073,036 discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

Japanese Kokai No. JA 56/92228 is directed to processes for producing highly pure alkylene glycols. The disclosure is directed to a distillation procedure for recovery of a molybdenum and/or tungsten containing catalyst from an alkylene oxide hydrolysis process in the presence of carbon dioxide. The application states that the catalyst is at least one compound selected from the group consisting of compounds of molybdenum and tungsten which compound may be in combination with at least one additive selected from the group consisting of compounds of alkali metals, compounds of alkaline earth metals, quaternary ammonium salts and quaternary phosphonium salts. The preferred catalysts are stated to be molybdic acid, sodium molybdate, potassium molybdate, tungstic acid, sodium tungstate and potassium tungstate. Potassium iodide is the only additive employed in the examples.

U.S. Pat. No. 4,551,566 discloses the production of monoalkylene glycols with high selectivity by the reaction of a vicinal alkylene oxide with water in the presence of a water soluble metavanadate. Hence, lower water to alkylene oxide ratios can be employed using the disclosed process with attractive selectivities to the monoglycol products. The counter ion to the metavanadate is selected to provide a water soluble metavanadate salt under the reaction conditions employed and alkali metals, alkaline earth metals, quaternary ammonium, ammonium, copper, zinc, and iron are suggested cations. It is also disclosed that the metavanadate may be introduced into the reaction system in the salt form or on a support such as silica, alumina, zeolites and clay. Since the metavanadate ion is water-soluble, it can be lost from the reaction system and means must be provided to recover it from the effluent from the reaction zone.

Unfortunately, insoluble salts of vanadate anion, such as calcium vanadate, as well as insoluble molybdate and other metalate salts do not appear to provide the selectivity toward the monoglycol products which is achievable with the water-soluble metalates. The problems with the recovery of the metalate are significant factors in considering the use of the technology on a commercial scale.

Japanese Kokai No. JA 57/139,026 discloses a process for the hydrolysis of alkylene oxides in the presence of carbon dioxide and a halogen-type anion exchange resin as a catalyst. The exemplified catalyst is a chlorine-type anion exchange resin (Dowex MSA-1(TM), a product of the Dow Chemical Company) and a similar iodine-type anion exchange resin. At a mole ratio of alkylene oxide to water of about 0.66, the selectivity to monoethylene glycol was reported to be 91.0 percent using the chlorine-type anion exchange resin and 89.6 percent using the iodine-type anion exchange resin. In the absence of carbon dioxide, the application disclosed that a selectivity to the monoethylene glycol of 34.8 percent was obtained and an unpleasant smell was noted in the product. In the absence of any anion exchange resin and in the presence of carbon dioxide, the selectivity to monoethylene glycol was reported to be 37.5 percent. All of the examples were conducted in an autoclave immersed in an oil bath at a temperature of 150° C. The disclosure reports that the maximum reaction liquid temperature was 130° C. and the reaction was carried out for 90 minutes. While the application did not specifically indicate the source of the unpleasant smell which originated in the comparative example where the carbon dioxide atmosphere was not employed, it could have been the result of degradation of the anion exchange resin.

U.S. Pat. No. 4,579,982 is directed to processes for the hydrolysis of alkylene oxide with enhanced selectivities to monoalkylene glycols using a reaction menstruum comprising an aqueous phase, a water-immiscible liquid phase and a metalate anion-containing material wherein the concentration of the metalate anion containing material in the water immiscible phase is greater than that in the aqueous phase.

Copending U.S. patent application Ser. No. 594,268, herein incorporated by reference, discloses a process for the hydrolysis of alkylene oxide to form the corresponding alkylene glycol in the presence of a selectivity enhancing metalate anion which is in association with electropositive complexing sites on a solid support. The selectivity-enhancing metalate anion is characterized as an anion containing a polyvalent metal having a double bonded oxygen thereon. The anion, in free-ionic form or in association with a solid support, enhances the selectivity of the hydrolysis reaction to the monoalkylene glycol. This application further discloses the hydrolysis can be conducted as a batch reaction or as a continuous process and that during the continuous process the hydrolysis can occur in one or several zones, all or some of which contain the metalate-containing solid support.

It is the purpose of the present invention to provide an improved process for the hydrolysis of alkylene oxide in the presence of a selectivity-enhancing metalate-containing solid catalyst which process provides a significantly more efficient use of the catalyst, without a significant loss in selectivity.

BRIEF DESCRIPTION OF THE INVENTION

This invention relates to an improved process for the hydrolysis of alkylene oxide to produce alkylene glycol which comprises:

(a) reacting alkylene oxide and water in the presence of a selectivity-enhancing amount of a selectivity-enhancing metalate containing solid, until about 90–95%, preferably about 93–94%, of the alkylene oxide is converted to alkylene glycol; and then (b) completing the hydrolysis reaction of (a) in the absence of the selectivity-enhancing metalate containing solid.

Preferably, the improved process for the hydrolysis of alkylene oxide to produce alkylene glycol comprises:

(a) reacting alkylene oxide and water in the absence of a selectivity enhancing metalate-containing solid, until about 10–35%, preferably about 20–30% and most preferably, about 27%, of the alkylene oxide is converted to alkylene glycol;

(b) continuing the hydrolysis reaction of (a) in the presence of a selectivity-enhancing amount of a selectivity-enhancing metalate containing solid, until about 90–95%, preferably 93–94% of the alkylene oxide is converted to alkylene glycol; and (c) completing the hydrolysis reaction of (b) in the absence of the selectivity-enhancing metalate-containing solid.

The process of this invention is significantly more efficient than the processes of the prior art and is particularly suitable for the production of monoalkylene glycols on a commercial scale in an economically attractive manner. For example, during the hydrolysis of ethylene oxide to form ethylene glycol using a selectivity-enhancing metalate-containing solid, such as a tungstate exchanged-anion exchange resin, as a catalyst throughout the entire hydrolysis reaction, the percentage of catalyst consumed depends on the percent of ethylene oxide converted. Using a plug flow reactor computer simulation program incorporated with a kinetic model of a tungstate exchanged-ion exchange catalyzed hydrolysis reaction, the following catalyst consumption/ethylene oxide conversion profile were calculated:

| Ethylene Oxide Conversion (%) | Percent of Catalyst Consumed at Each Step | Total Catalyst Consumed at Each Step |
|---|---|---|
| For an isothermal reaction: | | |
| 0–30 | 6% | 6% |
| 30–93 | 29% | 35% |
| 93– | 65% | 100% |
| For an adiabatic reaction: | | |
| 0–26 | 17% | 17% |
| 26–93 | 33% | 50% |
| 93– | 50% | 100% |

Accordingly, the process of this invention can decrease the amount of catalyst necessary by over 50% compared to the prior art process wherein catalyst is continuously present throughout the entire hydrolysis reaction. Furthermore and unexpectedly, this decrease in the amount of catalyst is accomplished without a significant decrease in selectivity. The process of this invention additionally enables the ratio of water to alkylene oxide to be reduced while achieving comparable, if not improved, selectivities to monoalkylene glycols over those achievable in conventional, commercial hydrolysis reactions.

Discussion of the Metalate Containing Solid

The alkylene oxide and water are contacted with a selectivity-enhancing metalate-containing solid which is a metalate in association with electropositive complexing sites on a solid substrate. The metalate is characterized by an anionic structure containing at least one polyvalent metal atom, M, having a positive functional oxidation state, e.g., often an oxidation state of at least +3, usually +4 to +7, and at least one oxygen ligand which is conventionally characterized as a double-bonded oxygen atom. The metalate anion can be illustrated by the following formula:

wherein q is the negative charge of the anion, which is usually between −1 and −4, A is one or more substituents to fill the remaining valencies (m) of M, and may be the same or different, and may be, for instance, double bonded oxygen; halogen (e.g., chlorine, fluorine, iodine); —O— or —S— wherein the remaining valency of the oxygen or sulfur atom is in free ionic form or is bonded to a metal atom (as in a bimetal or polymetal-containing metalate) or a counter ion, e.g., alkali metal, alkaline earth metal, ammonium, phosphonium and the like cations; or an organic radical, e.g., alkyl, aryl, acyl, alkoxy, amino, phosphino, etc. of 1 to about 12 carbons; and the like. Most commonly A is —O— or =O. Even when the A in the starting organometalate is other than —O—, e.g., chlorine, it is possible that the original substituent becomes replaced by —O— in the course of the process.

Particularly preferred metals for the metalate anions include the metals in groups Vb and VIb of the periodic chart such as vanadium, molybdenum and tungsten, although other metals may also find application. Representative metalate anions which are especially useful include molybdate, tungstate, metavanadate, hydrogen pyrovanadate and pyrovanadate; although because of the complex chemistry associated with many metalate anions, the precise structure of the operative specie or species may be different. Frequently, the metalate anion is an anion conventionally characterized by a formula such as $[MoO_4]^{2-}$, $[VO_3]^-$, $[V_2O_7H]^{3-}$, $[V_2O_7]^{4-}$, and $[WO_4]^{2-}$; however, it is recognized that the chemistry of these metalate anions, particularly the vanadates, is complex, and the exact chemical formula under the conditions of the process may prove to be different.

Not all metalate anions, including those of vanadium, tungsten and molybdenum, exhibit desired activity with alkylene oxide. For example, it has been observed that paramolybdate and paratungstate anions (as the added metalate anion) appear to exhibit less, if any, activity for enhancing selectivity.

However, in an aspect of the invention, the metal for the metalate anion is selected on the basis of the nucleophilicity and electrophilicity in the anion with respect to alkylene oxide in the environment. For example, the metal as in the metalate often has a nucleophilicity with respect to ethylene oxide greater than that exhibited by rhenium as rhenate anion under the same conditions. Also, it is frequently the case that the metal as the metalate has an electrophilicity with respect to ethylene oxide greater than that exhibited by vanadium in orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease, the cation may be sodium. If the rate and/or selectivity to the monoethylene glycol is less than that provided by the rhenate anion, then the metal as the metalate is probably less nucleophilic than rhenium in rhenate with respect to ethylene oxide. If the production of diethylene glycol and polyethylene glycol is greater than that provided with orthovanadate, regardless of the rate of formation of glycols, then the metal as the metalate is probably less electrophilic than orthovanadate with respect to ethylene oxide.

Because the selectivity-enhancing metalate anions enhance the selectivity of the hydrolysis to the monoalkylene glycol product, it is believed that an interaction or even chemical reaction occurs between the metalate anion and the alkylene oxide. See, for example, copending U.S. patent application Ser. No. 594,264, herein incorporated by reference. Any intermediate species formed between the metalate anion and alkylene oxide is believed to hydrolyze more rapidly to alkylene glycol than the rate at which it is formed. Thus, in the presence of water, the chemical determination of any intermediate species through techniques such as nuclear magnetic spectroscopy, is not presently feasible. Without being limited to theory, it is believed that advantageous metalate anions are those that are capable of interacting or reacting with alkylene oxide.

The electropositive complexing sites for association with metalate anion are on a water-insoluble support which may be organic or inorganic, i.e., the support is solid under the conditions of the reaction. The electropositive complexing sites and the water insoluble support are substantially non-reactive with water, alkylene oxide and alkylene glycol.

The preferred electropositive complexing sites and the water-insoluble supports are those whose degradation products do not adversely affect the quality of the alkylene glycol product or can be facilely removed from the alkylene glycol product.

Typical electropositive complexing moieties can contain strongly electropositive complexing groups such as quaternary ammonium groups, quaternary phosphonium groups, sulfonium groups, or arsonium groups or moderately electropositive complexing groups such as protonated tertiary amines and protonated tertiary phosphines. Because of the stability and availability of quaternary ammonium and tertiary amine groups, they are generally preferred.

Suitable electropositive complexing groups include those having the general formula:

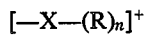

wherein X is nitrogen, phosphorous, sulfur, or arsenic, or tin bonded directly or indirectly to the support; and R may be the same or different and is hydrogen, monocyclic aryl or aralkyl of 6 to 8 carbon atoms, monocyclic alkaryl of 7 to 9 carbon atoms, or alkyl or alkoxy of 1 to about 6 carbon atoms, and R may be substituted with groups which are substantially non reactive with alkylene oxide, alkylene glycol, or water, e.g., hydroxy groups such as hydroxyalkyl substituents, haloalkyl substituents, silyl substituents, siloxy substituents, and the like; and n designates that sufficient R groups are provided to satisfy the remaining valencies of X, e.g., n is 3 and X is nitrogen when the electropositive complexing site is quaternary ammonium. In some cases, the stability of the electropositive complexing sites is enhanced when R is lower alkyl, especially methyl. It is also possible for X to be contained in a heterocyclic structure. Frequently, such cyclic structures contain 5 or 6 ring members with one or two members being the charge carrying center X.

The electropositive complexing site may be bonded to the solid support through, for example, an alkylene, arylene, silyl or siloxy group.

Solid supports having electropositive complexing sites include inorganic substrates, such as carbon, silica gel, zeolite, clay and glass beads. These supports may have the electropositive complexing sites affixed through adsorption, reaction or graft polymerization. See, for instance, Japanese Kokai Nos. 50/32085 and 52/26386. See also, P. Tundo, et al., "Anion Exchange Properties of Ammonium Salts Immobilized on Silica Gel," J. Am Chem. Soc., Vol. 104, pp 6547-6551 (1982), and P. Tundo, et al., "Phase-Transfer Catalysts Immobilized and Adsorbed on Alumina and Silica Gel", J. Am. Chem. Soc., Vol 104, pp 6551-6555 (1982). U.S. Pat. No. 4,430,496 discloses silyl alkylammonium sites on inert particles. See also German patent application No. 2,433,409. The above are all herein incorporated by reference.

Suitable supports for the electropositive complexing sites also include water-insoluble anionic resins. The resin can be varied to convenience and can comprise essentially any resinous composition. The resins include high molecular weight polymers and copolymers e.g., addition and condensation polymers, including polyalkylenes, polyesters, polycarbonates, polysulfones, polyimides, phenolic resins, formaldehyde resins, polyurethanes and the like, and the electropositive complexing sites may be adsorbed, reacted or grafted on the resin. While many available resins are carbon-based, silica-based resins may also find application in processes in accordance with this invention. These resins include organosiloxane polymers, such as dimethyl polysiloxane, methylphenyl polysiloxane, methylvinyl polysiloxane, cyanoalkylmethyl polysiloxanes and fluoroalkyl polysiloxanes. See, for example, U.S. Pat. No. 4,417,066, pertaining to organosiloxane polymers containing quaternary ammonium sites. U.S. Pat. No. 4,410,669 discloses polymeric ammonium compounds with a silica-type backbone which are said to exhibit good thermal stability and inertness to chemical attack. Both of these patents are herein incorporated by reference.

Monomers which can be employed in preparing carbon-based resins include styrene and styrene derivatives such as methylstyrene, ethylstyrene, vinylnaphthalene, 3,4,6-trimethylstyrene, chlorostyrene, methoxystyrene, N,N-dimethylaminostyrene, nitrostyrene, chlorostyrene, trifluorostyrene, trifluoromethylstyrene and aminostyrene; butadiene; acrylonitrile and acrylonitrile derivatives; acrylic acid and acrylates such as methyl acrylate and chloromethyl acrylate; methacrylic acid and methacrylates such as cyclohexyl methacrylate, dimethylaminoethyl methacrylate, glycidyl methacrylate and methyl methacrylate; maleates such as diethyl maleate; fumarates such diethyl fumarate; vinyl ketones such as methyl vinyl ketone and ethyl isopropyl ketone; vinylidienes; acrylamide and acrylamide derivatives; aliphatic acid vinyl esters such as vinyl acetate, vinyl butylate and vinyl caproate; formaldehyde with, e.g., phenol, xylene, urea, melamine; bisphenol A; sulfones such as dichlorodiphenyl sulfone; phosgene; toluene diisocyanate; polyols such as ethylene glycol; and epoxybutadiene; etc.

For purposes of strength and chemical resistance, the resin is preferably cross-linked. Representative resins which can be cross-linked include styrene-divinylbenzene, styrene-glycol dimethacrylate, aniline-formaldehyde, aryl polyamine-formaldehyde, phenol-formaldehyde, polyacrylate, and the like. Generally, the amount of cross-linking agent provided is an amount of about 4 or 5 to 30 or 40 mole percent based on the monomer used to prepare the resin.

Cross-linking agents which can be employed in preparing resins include divinylbenzene, divinyltoluene, divinylnaphthalene, divinylethylbenzene, trivinylbenzene, divinyldiphenylmethane, divinylbenzyl, divinylsulfone, divinylketone, bis(vinylpyridinoethyl) ethylene diamine, diallyl phthalate, triallylamine, N,N'-ethylenediacrylamide, ethylene glycol dimethacrylate, triethylene glycol dimethacrylate, trimethylolpropane trimethacrylate, trimethylolpropane triacrylate, triallyl isocyanurate and diallyl melamine.

The resins can take many forms, such as swellable gels, semi-porous or iso-porous resins, or macro-porous (macro-reticular) resins. The resins may be spherical or irregular granules which in turn may be supported on a larger solid structure. Frequently, the major dimension of the resins is about 0.1 to 5 millimeters (e.g., 0.3 to 1 or 2 millimeters).

Anion exchange resins having quaternary amine sites and tertiary amine sites are commercially available. These resins include resins with acrylic matrices such as Amberlite (TM) IRA 68, IRA-60, and XE-258 resins available from Rohm & Haas Co.; phenolic-containing matrices such as Amberlite (TM) IRA-4B resin available from Rohm & Haas Co.; styrene divinylbenzene matrices such as Amberlite (TM), IR-900, IRA-904, IRA 93, IRA-94, and IRA 400 resins available from Rohm & Haas Co., Dowex (TM) 1, 2, 11, WGR, MSA 1, and MWA 1 resins available from the Dow Chemical Company, and Duolite (TM) A 101, A-102, and A-114, available from the Diamond Shamrock Corp.

Preferably, the support has at least about 0.1, e.g., 0.5 to 10, say 0.5 to 5 milli-equivalents of exchange capacity (based on the pendant electropositive complexing sites) per gram of dry support. It is at these sites that the association occurs between the metalate anion and the insoluble support.

The association of the metalate with the electropositive complexing sites on the insoluble support may be provided in any convenient manner. Usually the placing of the metalate on the insoluble support is accomplished by a loading technique whereby a soluble metalate salt is contacted in solution in an inert liquid medium with the insoluble support to displace original anion at the site.

The counter ions to the metalates useful in preparing the solid supported metalates used in this invention are preferably water-soluble, include alkali metals, alkaline earth metals, ammonium ion, copper, zinc, iron, quaternary ammonium cations, quaternary phosphonium cations, sulfonium cations, and other cations.

Inert liquid media often include water, aliphatic and aromatic hydrocarbons and substituted hydrocarbons such as hexane, benzene, toluene, xylene, o-dichlorobenzene, methylene chloride, chloroform, carbon tetrachloride, and the like.

The loading can occur at any temperature at which the metalate is dissolved. The temperature employed is preferably below that which results in unduly adverse effects to the reactants. Usually, the temperature will be about 0° C. to 120° C., say, about 15° C. to 100° C. Any convenient pressure may be employed, and subatmospheric pressures may assist in the dispersion of the metalate anion throughout the support. The loading process is typically conducted under a suitable atmosphere which frequently may be a substantially inert atmosphere, such as air or nitrogen, for a sufficient period of time to enable desired amounts of metalate anion to become associated with the electropositive complexing sites. This period of time will generally vary with the method, reagents and conditions employed, but it will often be about 0.5 to 50, say about 1 to 15 hours. The resulting product containing the metalate may be recovered by any convenient physical separation technique, such as filtering, decanting and evaporating.

In order to obtain the desired metalate in association with the electropositive complexing sites on the insoluble support, it is not necessary to use the metalate form. Indeed, any form of the metal which will yield the metalate by reaction subsequent to the loading, including in situ during the hydrolysis reaction, is believed to be suitable. The metal-containing anions may therefore contain halide, e.g., chloride and iodide; sulfide, aliphatic or aromatic hydrocarbon, or similar substituents. The selection of the metalate or precursor of the metalate will, in general, be dependent upon the availability of the compound and its processing characteristics in order to form the association with the electropositive complexing sites of the insoluble support and, in the case of the precursors to the metalate, additionally the ability to form the desired product.

Typically during loading, the mole ratio of metalate ion to the electropositive complexing sites is between about 1:100 to about 100:1, and frequently is between about 1:1 to 25:1. In the prepared product with the associated metalate anion, the ratio of electropositive complexing sites having associated metalate anion to total electropositive complexing sites is frequently between about 1:10 to 1:1, preferably about 0.9:1 to 1:1. It has generally been noted that even though the metalate anion may have a negative charge of two or more, such as molybdate and tungstate, the metalate anion may be associated with only one electropositive complexing site. Typically, the metalate loaded support comprises, as determined by conventional elemental analysis, at least about 0.1, and preferably at least about 1, often about 2 to 30, say, 5 to 25, weight percent of the metal of the metalate (metal basis) based on total weight of the dry support. The saturation of the electropositive complexing sites of the insoluble support is the only limitation upon the maximum weight percent of metalate contained in association with the electropositive complexing sites on the insoluble support. It is generally desired to achieve as close to saturation levels as possible for reasons of activity and life. Moreover, it is also believed that the association of the metalate anion with the electropositive complexing sites assists in stabilizing the electropositive complexing sites under hydrolysis conditions. This is particularly important when a decomposition of the electropositive complexing sites results in adverse effects to the desired alkylene glycol product. For instance, when using quaternary amine-containing anionic exchange resins, the degradation of the resin may yield amines which can provide an odor to the alkylene glycol product.

Discussion of the Production of Alkylene Glycols

Vicinal alkylene oxides which may be used to produce alkylene glycols have the general formula:

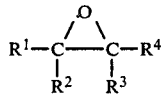

wherein $R^1$, $R^2$, $R^3$ and $R^4$ are the same or different and are hydrogen or hydrocarbyl-containing substituents of 1 to about 20 carbon atoms. Often $R^1$, $R^2$, $R^3$ and $R^4$ are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms. Representative of alkylene oxides are ethylene oxide, propylene oxide, butylene oxide, including isobutylene oxide, 1,2-butylene oxide and 2,3-butylene oxide, pentylene oxide, styrene oxide, cyclohexene oxide and the like. Preferably, the alkylene oxide is an aliphatic alkylene oxide having 2 or 3 carbon atoms, i.e., ethylene oxide and propylene oxide.

Alkylene oxides are well known, as is their preparation. For example, alkylene oxide can be prepared by reacting an olefin with an organo hydroperoxide in the presence of a catalyst or by the partial oxidation of alkylene (especially ethylene) with a molecular oxygen containing gas in the presence of a silver catalyst. Frequently, the alkylene oxide has been purified to avoid the presence of components which may produce troublesome impurities in the alkylene glycol product from the hydrolysis.

Water is employed as a co-reactant for the formation of the corresponding alkylene glycol and is preferably provided as a liquid although steam may be used. Usually the water is of sufficient purity to provide a suitable quality alkylene glycol product. The water may be distilled or demineralized, for example, by ion exchange treatment.

In the processes of this invention, the mole ratio of water based on the alkylene oxide as provided to the reaction zone is generally at least about 0.1. However, it is desirable to maintain at least a slight molar excess of water over the amount of water required for reaction with the alkylene oxide on a stoichiometric basis to ensure a higher selectivity of alkylene oxide to the monoalkylene glycol product. The mole ratio may be greater than 50, but such high ratios often prove to be commercially unattractive because of the energy required to recover the alkylene glycol. Typically, the mole ratio of water to alkylene oxide is between about 1:1 and 40:1, say between about 1:1 and 30:1 and, when high selectivities to the monoalkylene product are desired, the ratio is preferably at least about 5:1 to 30:1.

As stated above, in the preferred embodiment of this invention, the alkylene oxide and water are initially reacted in the absence of any selectivity-enhancing catalyst until about 10-35%, preferably about 20-30% and most preferably about 27%, of the alkylene oxide is converted to alkylene glycol.

In the next step of the preferred embodiment of the process of this invention, a selectivity-enhancing amount of a selectivity-enhancing metalate-containing solid is introduced into the reaction mixtures comprising residual alkylene oxide, water and alkylene glycol. The reaction of alkylene oxide and water is continued until about 90-95%, preferably about 93-94%, of the alkylene oxide is converted to alkylene glycol (including the 10-35% alkylene glycol formed in the initial step above).

In the final step, the reaction mixture comprising residual alkylene oxide, water and alkylene glycol is removed from the presence of the metalate-containing solid. The reaction of the residual alkylene oxide and water is then continued to completion in the absence of the metalate-containing solid.

The determination of the percentage of alkylene oxide converted to alkylene glycol at each step can be conducted by any convenient procedure known in the art, such as by gas chromatography analysis.

The methods utilized for introduction and removal of the metalate-containing solid can vary and will be determined largely by the nature of the hydrolysis process utilized. The process of this invention can be conducted as a batch process or, preferably, as a continuous process. In a continuous process the various steps of the process of this invention are conducted in multiple separate contiguous reaction zones within a single reactor or in a sequential series of multiple reactors. The alkylene oxide and water reactants, which may or may not be previously admixed, are introduced into a reactor which may be maintained under isothermal, adiabatic or hybrid conditions. In accordance with the process of this invention, the hydrolysis occurs sequentially in more than one reactor or reaction zone, one or more of which contains the metalate-containing solid and one or more of which does not contain the metalate containing solid.

In a multiple reactor system, a different type of reactor is preferably employed for each step. For example, in the first step of the preferred embodiment of the process of this invention, a small diameter cylinder can be used to minimize back mixing of the alkylene oxide/water reactant mixture. The diameter of this cylinder is, generally, in the range of 1 to 4 feet. In the second step of the preferred embodiment of the process of this invention, a fluid-solid catalytic unit can be used. The metalate-containing solid is retained in a fixed bed position in the reactor with the alkylene oxide/water/alkylene glycol reactant mixture flowing through the catalyst bed. The reactor for this second step can be a large cylinder with jacketed or internal-coil cooling or the reactor can be a cylindrical container containing multiple tubes inside. The third step of the preferred embodiment of this invention is conducted in a tank or a large diameter cylinder to maximize the resident time of the alkylene oxide/water/alkylene glycol mixture.

In a single reactor system with multiple reaction zones, a fixed bed reactor is preferably used. For example, in the preferred embodiment of the process of this invention, an inert solid such as an alpha-alumina pill can be packed in the first reactor zone to minimize the back mixing of the alkylene oxide/water reactant mixture. The second reaction zone contains the metalate-containing solid with jacketed or internal coil cooling used as needed. The third reaction zone is simply an empty section of the reactor.

It is to be understood that when the two-step process of this invention is utilized instead of the three-step process, only the second and third reactor or reaction zones described above need be used.

Generally, the mole ratio of metalate sites to alkylene oxide in the reactor or reaction zone is at least about 0.0001:1, and is often at least about 0.01:1. (Although certain metalate anions are believed to have more than one site which can associate with alkylene oxide, e.g., tungstate and molybdate; for purposes of this discussion, the moles of metalate sites shall be calculated as the moles of metalate anion.) In some instances it may be desired to provide the metalate sites in an amount greater than that required on a stoichiometric basis for reaction with the alkylene oxide present in the reaction zone. Thus, the mole ration of metalate sites to alkylene oxide in the reaction zone can be 20:1 or even 50:1 or greater. Because of the volume of reactor and amount of metalate required, economics usually dictate that the mole ration of metalate sites to alkylene oxide will be within the range of about 0.01:1 to 20:1, say, about 0.05:1 to 15:1. Since with some metalate anions the reaction to alkylene glycol can proceed very quickly (and thereby the metalate anions are available for further interaction with alkylene oxide), a less than stoichiometric amount of metalate anion may still provide desirable selectivities to monoalkylene glycol. Typically, the pH is maintained between about 5 and 11, preferably about 6 to 10.5, and most often the pH is in the range of about 6 to 10.

With some metalate anions, such as the vanadates, tungstates and molybdates, the pH of the medium can be determinative of the specie present. For example, in strong bases, the orthovanadate may predominate, but at neutral conditions, metavanadate will exist. In another example, more acidic media promote the formation of polynuclear molybdates which often have less, if any, beneficial effect in enhancing selectivity.

The pH can be maintained within the desired range by the addition of acid or base, or the addition of buffers, as is well known in the art; however, the presence and nature of salts should be considered since displacement of the metalate anion from the electropositive complexing site can occur resulting in the loss of the metalate anion. Mechanisms which have been proposed for maintaining the desired pH include the addition of carbon dioxide or inorganic acids or organic acids such as sulfuric acid, hydrochloric acid and acetic acid. The agents for maintaining the pH value of the reaction menstruum can be added in any convenient manner such as during the reaction, e.g., by purging with carbon dioxide, or by addition to one or more of the reactants prior to introducing the reactants into the reactor. For example, the pH of the water component can be adjusted to the desired level prior to admixing with the alkylene oxide.

The maintenance of the pH within the desired ranges can also have a secondary effect of enhancing the stability of the association between the metalate and the electropositive complexing site, and enhancing the stability of the solid support, e.g., anion exchange resin. Thus, even brief excursions into high pH ranges, e.g., pH values greater than 11, should generally be avoided.

The process is carried out at temperatures sufficient to enable the selectivity-enhancing effect of the metalate anion to be achieved. The benefits of the metalate anion are believed to be achievable at low temperatures, but the rate of production of alkylene glycol may be undesirably low. The temperature, however, should not be so high that the electropositive complexing sites and/or the insoluble support and/or the metalate anion are unduly adversely affected. Accordingly, the process is often carried out at a temperature between about 20° C. and about 200° C. With the use of many anion exchange resins, temperatures greater than about 140° C. or 150° C. are generally avoided because of potential deterioration of the pendant active groups. Most often, the reaction is carried out at a temperature between about 50° C. and 140° C., say, about 80° C. to 130° C. or 140° C.

As disclosed in U.S. Pat. No. 4,579,983, herein incorporated by reference, the stability of the electropositive complexing sites is believed to be enhanced by the addition of small quantities of metalate anion to the reaction mixture. This metalate anion is believed to replace any metalate anion lost from the electropositive complexing sites during the course of the reaction. Often, the amount of metalate anion provided can be relatively small, e.g., less than 1,000 ppm by weight based on the reactants fed to the reaction zone, say, about 1 to 1000, e.g., about 50 to 250, ppm by weight. Often, the mole ratio of metalate anion added to metalate anion in association with the electropositive complexing sites is less than 1:20, say 1:50 to 1:1000.

The metalate anion can be provided as any convenient, dissociatable metalate anion-containing material. Thus, the metalate anion-containing material is frequently a water-soluble acid or salt, i.e., the cations include hydrogen, alkali metals, alkaline earth metals, ammonium ion, copper, zinc, iron, quaternary ammonium cations, quaternary phosphonium cations, sulfonium cations, and the like. Conveniently, the cation is sodium or potassium due to its ready availability. However, in some instances it is desirable to employ an organic-containing cation to facilitate its separation from the alkylene glycol product by extraction into a water immiscible phase in which it is preferentially soluble. See for further discussion U.S. Pat. No. 4,571,440, herein incorporated by reference. The recovery of metalate cations can also be effected by, say, an anion exchange solid such as disclosed in U.S. Pat. No. 4,560,813, herein incorporated by reference.

The metalate anion need not be the same as the metalate anion initially in association with the electropositive complexing sites; however, the initial metalate anion will tend to be replaced by the metalate anion added. Consequently, the metalate anion added is usually the same as the initial metalate anion.

The pressure can be subatmospheric, atmospheric or above atmospheric. The process is usually carried out at a pressure sufficient to maintain the reactants in the liquid phase. For purposes of convenience, the reaction is typically conducted at pressures greater than ambient, e.g., between about 0.1 and 1,000 kilograms per square centimeter gauge and preferably between about 2 and 100 kilograms per square centimeter gauge.

The production of alkylene glycol according to this invention can be conducted in the presence of a gas, which is preferably inert. Gases which can be employed include air, carbon dioxide, nitrogen, argon and the like. Carbon dioxide is often present during the hydrolysis of alkylene oxide by the very nature of the process and the source of the alkylene oxide (especially ethylene oxide by partial oxidation of ethylene). Frequently, it is desired to maintain the mole ratio of carbon dioxide to alkylene oxide less than 0.1:1, particularly less than 0.05:1. Carbon dioxide can be used in certain amounts to enhance the selectivity provided by vanadate anion such as disclosed in U.S. Pat. No. 4,578,524, herein incorporated by reference.

The process can be conducted in the presence of a solvent which does not unduly adversely affect the solid support, the electropositive complexing sites, the metalate anion, alkylene oxide or alkylene glycol.

The hydrolysis reaction is exothermic, and, hence, the temperature of the incoming reactants and the heat transfer abilities from the reactor affect the temperatures achieved within a reactor. Similarly, the unreacted and excess reactants and other components of the reaction medium, such as solvents, serve as a heat sink. Some or all of the material passing to a subsequent reactor or zone can be cooled to remove heat and control temperature.

Conventional hydrolysis reactors are substantially adiabatic and enable high temperatures for evaporating water for the recovery of alkylene glycol to be achieved. Since it may be beneficial from the standpoint of maintaining the stability of the metalate anion association, the electropositive complexing sites and the support, isothermal reactors may be preferred. Moreover, since the constant temperature used in an isothermal reactor can be greater than the inlet temperature to an adiabatic reactor, the amount of metalate anion required may be less than that required in an adiabatic reactor.

The reaction for each step in the process of this invention is conducted for a period of time sufficient to convert the necessary percent of alkylene oxide, for each step in the process as described above.

The alkylene glycol can be recovered from the reaction effluent in any convenient manner. Typically, the water is removed in a series of multiple-effect evaporators and the alkylene glycol is further refined by vacuum distillation.

The following examples are presented to illustrate the present invention but the examples are not intended to limit the scope of the invention.

EXAMPLES

A computer simulation model was employed to generate the following examples. A kinetic model for the hydrolysis of ethylene oxide to produce ethylene glycol in a plug flow reactor was developed and incorporated in a computer program. A plug flow reactor is characterized by the fact that the residence time in the reactor is the same for all elements of the fluid. The model included the non-catalyzed hydrolysis reaction mechanism and a molybdate/tungstate-exchanged ion exchange catalyzed hydrolysis reaction mechanism. The computer program predicted the degree of conversion, the temperature and the distribution of reaction products along the length of the reactor, as a function of the inlet composition, flow rate, temperature and the dimensions of the reactor.

The computer program consisted of four subroutines. These subroutines, in brief, were as follows.

1. MAIN a. Read input data.
b. Initialized variables.
c. Calculated the portion of the rate constant which were independent of temperature and concentration.
d. Calculated conversion, product distribution, and other output variables.
e. Printed output results.

2. Glycol a. Computed differential rate of change in the flow rate of all components at each step.
b. Computed differential rate of change in contact time at each step.
c. Computed differential rate of change in temperature at each step.

3. Prop a. Calculated heat capacity of reacting mixtures as a function of temperature and component flow rate.
b. Calculated volumetric flow rate of reacting mixture as a function of temperature and component flow rate.

4. RKDE

Classical fourth order Runge Kutta integration method with fixed step.

COMPARATIVE EXAMPLE A

This example demonstrates the production of di-ethylene glycol from ethylene oxide hydrolysis under a conventional non-catalyzed system. The computer simulation was of an ethylene oxide hydrolysis reaction conducted as follows:

A mixture of water and ethylene oxide at a 24.4/1 mole ratio (122° C.) is charged to an adiabatic plug flow reactor (4'I.D×120') at a flow rate of 660,000 lb/hr. The pressure inside the reactor is 200 psig. The di-ethylene glycol formation rate is determined and plotted against the percent ethylene oxide converted (see Table 1 and FIG. 1 below). The di-ethylene glycol formation rate is calculated by the model described above and is expressed in units of lb. mole/hr/ft.

TABLE 1

| Ethylene Oxide Conversion (%) | Diethylene Glycol Formation Rate (lb. mole/hr/ft.) |
|---|---|
| 1. 11.73 | 0.196 |
| 2. 26.0 | 0.516 |
| 3. 43.2 | 0.933 |
| 4. 62.7 | 1.447 |
| 5. 80.7 | 1.417 |
| 6. 92.4 | 0.813 |
| 7. 97.5 | 0.310 |
| 8. 99.2 | 0.099 |

FIG. 1 is a plot of the calculated di-ethylene glycol (DI) formation rate vs. the ethylene oxide (EO) conversion.

The plot in FIG. 1 shows that the majority of di-ethylene glycol (DI) formation during the hydrolysis reaction occurs at ethylene oxide (EO) conversions between about 20 percent and about 97 percent.

COMPARATIVE EXAMPLE B

This example demonstrates the selective production of monoethylene glycol from ethylene oxide hydrolysis using a tungstate exchanged-ion exchange catalyst throughout the entire hydrolysis reaction. The computer simulation was of an ethylene oxide hydrolysis reaction conducted as follows:

A mixture of water and ethylene oxide at a 24.4/1 mole ratio is charged to a plug flow reactor (180'×4'I.D.) containing 102,400 lb. of a tungstate-loaded Dowex MSA 1 resin. Dowex MSA-1 resin is a polystyrene-based anion exchange resin available from Dow Chemical Company, Midland, Mich. The water and ethylene glycol are charged to the reactor at a flow rate of 660,000 lb/hr. The pressure inside the reactor is 200 psig and the temperature inside the reactor was 125° C. The amount of ethylene oxide converted and the selectivity to monoethylene glycol is determined (see Table 2 below).

EXAMPLE 1

The same procedure as described in Comparative Example B is used except that the reactor consists of 3 reaction zones: (1) The first reaction zone is 50'×4'I.D. and contains no catalyst; (2) The second reaction zone is 50'×4'I.D. and contains 28,500 lb of the tungstate-loaded DOWEX MSA 1 resin; and the third and final zone is 100'×4'I.D. and contained no catalyst. The temperature in the first reaction zone is 125° C.; in the second reaction zone is 125° C.; and in the third reaction zone is 155° C. Because of the three separate reaction zones, the hydrolysis reaction is catalyzed only at ethylene oxide conversions between 27 percent and 93 percent. The amount of ethylene oxide converted and the selectivity to monoethylene glycol are determined (see Table 2 below).

TABLE 2

| Example | Ethylene Oxide (Wt %) | Water (Wt %) | Resin Type/ Metalate Loaded | Amt. of Resin (lb.) | Catalyzed Reactor Length | Flow Rate (lb/min) | Reactor Temp °C. | EO Converted | MEG Selectivity |
|---|---|---|---|---|---|---|---|---|---|
| Comparative B | 9.1 | 90.9 | DOWEX MSA-1/ TUNGSTATE | 102,400 | 180 ft. | 11,000 | 125 | 99.9+ | 98.9 |
| 1 | 9.1 | 90.9 | DOWEX MSA-1/ TUNGSTATE | 28,500 | 50 ft. | 11,000 | 125 | 99.9+ | 97.3 |

Comparative Example B and Example 1 demonstrate that the selectivity to monoethylene glycol using the process of this invention (i.e., Example 1) compares favorably to the prior art process which utilizes catalyst throughout the entire hydrolysis reaction (i.e. Comparative Example B) and that the process of this invention requires significantly less catalyst (less than one third).

While this invention has been described with reference to certain specific embodiments, it will be recognized by those skilled in the art that many variations are possible without departing from the scope and spirit of the invention and it will be understood that it is intended to cover all changes and modifications to the invention disclosed herein for the purpose of illustration which do not constitute departures from the spirit and scope of the invention.

What is claimed is:

1. A process for the hydrolysis of alkylene oxide to produce alkylene glycol which comprises:
   (a) reacting the alkylene oxide and water in the presence of a selectivity-enhancing amount of a selectivity-enhancing metalate containing solid, until about 90 percent to about 95 percent of the alkylene oxide is converted to alkylene glycol; and
   (b) completing the hydrolysis reaction of (a) in the absence of the selectivity-enhancing metalate-containing solid.

2. A process as recited in claim 1 wherein step (a) is conducted until about 93 percent to about 94 percent of the alkylene oxide is converted to alkylene glycol.

3. A process as recited in claim 1 wherein the alkylene oxide is ethylene oxide.

4. A process as recited in claim 3 wherein the alkylene glycol is monoethylene glycol.

5. A process as recited in claim 1 wherein the metalate anion in the metalate-containing solid is represented by the formula:

$$[(A)_m M(O)]^{-q}$$

wherein M is a polyvalent metal atom having a positive functional oxidation state, q is the negative charge of the metalate anion, and A is one or more substituents to fill the remaining valencies (m) of M and is selected from the group consisting of double bonded oxygen and —O— wherein at least one A is —O—.

6. A process as recited in claim 5 wherein the electropositive complexing sites in the metalate-containing solid are represented by the formula:

$$[-X-(R)_n]^+$$

wherein X is nitrogen, phosphorous, sulfur, or arsenic bonded directly or indirectly to the support, each R may be the same or different and is hydrogen, monocyclic aryl or aralkyl of 6 to 8 carbon atoms, monocyclic aralkyl of 7 to 9 carbon atoms, or alkyl or alkoxy of 1 to about 6 carbon atoms and n designates that sufficient R groups are provided to satisfy the remaining valencies of X.

7. A process as recited in claim 6 wherein the metalate anion comprises at least one of molybdate, tungstate, metavanadate, hydrogen pyrovanadate, and pyrovanadate.

8. A process as recited in claim 7 wherein the solid support in the metalate-containing solid comprises an anion exchange resin.

9. A process as recited in claim 8 wherein the metalate-containing solid is a tungstate-exchanged anion exchange resin.

10. A process for the hydrolysis of alkylene oxide to produce alkylene glycol which comprises:
    (a) reacting alkylene oxide and water in the absence of a metalate-containing solid, until about 10 percent to about 35 percent of the alkylene oxide is converted to alkylene glycol;
    (b) Continuing the hydrolysis reaction of (a) in the presence of a selectivity-enhancing amount of a selectivity enhancing metalate-containing solid, until about 90 to about 95 percent of the alkylene oxide is converted to alkylene glycol; and
    (c) completing the hydrolysis reaction of (b) in the absence of the selectivity-enhancing metalate-containing solid.

11. A process as recited in claim 10 wherein step (a) is conducted until about 20 percent to about 30 percent of the alkylene oxide is converted to alkylene glycol.

12. A process as recited in claim 10 wherein step (a) is conducted until about 27 percent of the alkylene oxide is converted to alkylene glycol.

13. A process as recited in claim 10 wherein step (b) is conducted until about 93 to about 94 percent of the alkylene oxide is converted to alkylene glycol.

14. A process as recited in claim 10 wherein the alkylene oxide in ethylene oxide.

15. A process as recited in claim 10 wherein the alkylene glycol is monoethylene glycol.

16. A process as recited in claim 10 wherein the metalate anion in the metalate-containing solid is represented by the formula:

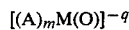

wherein M is a polyvalent metal atom having a positive functional oxidation state, q is the negative charge of the metalate anion, and A is one or more substituents to fill the remaining valencies (m) of M and is selected from the group consisting of double bonded oxygen and —O— wherein at least one A is —O—.

17. A process as recited in claim 16 wherein the electropositive complexing sites in the metalate-containing solid are represented by the formula:

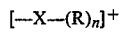

wherein X is nitrogen, phosphorus, sulfur, or arsenic bonded directly or indirectly to the support, each R may be the same or different and is hydrogen, monocyclic aryl or aralkyl of 6 to 8 carbon atoms, monocyclic aralkyl to 7 to 9 carbon atoms, or alkyl or alkoxy of 1 to about 6 carbon atoms and n designates that sufficient R groups are provided to satisfy the remaining valencies of X.

18. A process as recited in claim 17 wherein the metalate anion comprises at least one of molybdate, tungstate, metavanadate, hydrogen pyrovanadate, and pyrovanadate.

19. A process as recited in claim 18 wherein the solid support in the metalate-containing solid comprises an anion exchange resin.

20. A process as recited in claim 10 wherein the metalate-containing solid is a tungstate-exchanged anion exchange resin.

* * * * *